United States Patent
Jung et al.

(10) Patent No.: US 9,527,861 B2
(45) Date of Patent: Dec. 27, 2016

(54) PRODUCTION METHOD FOR ANHYDRO SUGAR ALCOHOL HAVING MARKEDLY REDUCED ION CONTENT AND IMPROVED COLOUR CHARACTERISTICS

(71) Applicant: SAMYANG CORPORATION, Seoul (KR)

(72) Inventors: Young Jae Jung, Seoul (KR); Jin Kyung Kim, Daejeon (KR); Do Hyun Kyung, Daejeon (KR); Hoon Ryu, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 32 days.

(21) Appl. No.: 14/399,026

(22) PCT Filed: May 9, 2013

(86) PCT No.: PCT/KR2013/004074
§ 371 (c)(1),
(2) Date: Nov. 5, 2014

(87) PCT Pub. No.: WO2013/169028
PCT Pub. Date: Nov. 14, 2013

(65) Prior Publication Data
US 2015/0094477 A1    Apr. 2, 2015

(30) Foreign Application Priority Data
May 11, 2012    (KR) .................. 10-2012-0050188

(51) Int. Cl.
C07D 493/04    (2006.01)
C07C 29/08    (2006.01)

(52) U.S. Cl.
CPC ............. *C07D 493/04* (2013.01); *C07C 29/08* (2013.01)

(58) Field of Classification Search
CPC .............................. C07D 493/04; C07C 29/08
USPC .......................................................... 549/464
See application file for complete search history.

(56) References Cited

U.S. PATENT DOCUMENTS 6,864,378 B2 * 3/2005 Bhatia ........................... 549/464
7,122,661 B2 * 10/2006 Fleche ................. C07D 493/04
536/124
8,236,973 B2 * 8/2012 Liu et al. ...................... 549/488
2003/0097028 A1 5/2003 Fuertes
2004/0110969 A1 6/2004 Fleche et al.
2004/0152907 A1 8/2004 Moore et al.
2007/0213544 A1 9/2007 Sanborn

FOREIGN PATENT DOCUMENTS

JP          2005-509667 A      4/2005
KR          10-0772255 B1     11/2007
KR       10-2011-0076268 A     7/2011
WO        WO 0239957 A2 *      5/2002

OTHER PUBLICATIONS

Çeçen, F., 1992, "Activated carbon." Kirk-Othmer encyclopedia of chemical technology p. 1-34.*
Calgon CP 12×40 Data Sheet 2015. p. 1-2.*
Flèche et al., "Isosorbide Preparation, Properties and Chemistry", starch/stärke, 1986, vol. 38, No. 1, pp. 26-30.
International Search Report, issued in PCT/KR2013/004074, dated Aug. 28, 2013.
Bock et al., "Acid Catalyzed Dehydration of Alditols. Part I. D-Glucitol and D-Mannitol", Acta Chemica Scandinavica, vol. 35B, 1981, pp. 441-449.
Fletcher et al., "Chemical Method for the Determination of Penicillin", J. Am. Chem. Soc., vol. 67, No. 6, Jun. 1945, pp. 1042-1043.
Kurszewska et al., "The Solvent-Free Thermal Dehydration of Hexitols on Zeolites", Carbohydrate Research, vol. 337, No. 14, 2002, pp. 1261-1268.

* cited by examiner

*Primary Examiner* — Samantha Shterengarts
*Assistant Examiner* — Matt Mauro
(74) *Attorney, Agent, or Firm* — Birch, Stewart, Kolasch & Birch, LLP

(57) ABSTRACT

The present invention relates to a production method for an anhydro sugar alcohol having a markedly reduced ion content and improved color characteristics, and, more specifically, relates to a method for producing an anhydrous sugar alcohol having a markedly reduced ion content, markedly lowered electrical conductivity and improved color characteristics, which is obtained by subjecting hydrogenated sugar (sugar alcohol) to a dehydration reaction and thereby converting same to an anhydrous sugar alcohol and then subjecting distilled water, which has been isolated through a distillation step, to a decolorizing process using activated carbon, and subsequently bringing the resulting decolorized substance into contact with an ion exchange resin.

9 Claims, No Drawings

PRODUCTION METHOD FOR ANHYDRO SUGAR ALCOHOL HAVING MARKEDLY REDUCED ION CONTENT AND IMPROVED COLOUR CHARACTERISTICS

TECHNICAL FIELD

The present invention relates to a method for producing anhydrosugar alcohols having remarkably reduced ion content and improved color property, and more specifically a method for producing anhydrosugar alcohols having remarkably reduced ion content, remarkably low conductivity and improved color property by converting hydrogenated sugar (sugar alcohol) to anhydrosugar alcohol by dehydration reaction, distilling the resulting liquid to isolate the distillate therefrom, decolorizing the distillate with active carbon, and subsequently contacting the decolorized product with ion exchange resins.

BACKGROUND ART

Hydrogenated sugar (also referred to as "sugar alcohol") means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

Anhydrosugar alcohol has a dial form with two hydroxyl groups in the molecule, and can be produced by using hexitol derived from starch. Because anhydrosugar alcohol is an environmentally friendly material derived from recyclable natural resources, it has received much interest for a long time and researches on its production have been proceeding. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like PET, polycarbonate, polyurethane, etc., and improve the strength of such materials. Furthermore, because anhydrosugar alcohol is a biodegradable, environmentally friendly material, it is very useful in the plastics industry. It is also known that anhydrosugar alcohol can be used as an adhesive, environmentally friendly plasticizer, biodegradable polymer, and environmentally friendly solvent for water-soluble lacquer.

In particular, because of its diol form with two hydroxyl groups in the molecule, anhydrosugar alcohol is very valuable as a property modifier in the plastics industry. The ion content and color of anhydrosugar alcohol are important factors influencing the physical, chemical and optic properties during polymerization in the plastics industry.

As such, anhydrosugar alcohol is receiving much interest because of its wide applicability. However, there have been few cases of practically using it industrially so far. This is because the conventional methods of producing anhydrosugar alcohol have limitations of high cost for the catalyst used in the dehydration reaction, low conversion rate, and low yields of distillation and purification, etc.

In the case of producing anhydrosugar alcohol by dehydrating hexitol and distilling the converted reaction liquid, depending on the dehydration reaction and the distillation condition, various byproducts as well as the desired anhydrosugar alcohol are generated, and formation of polymer materials also increases (Starch/Starke, vol. 38, pp. 26-30). In addition, the color becomes dark due to carbonization of hexitol or formation of another coloring substance(s), characteristics of which are not clearly known, and thus decolorization becomes difficult.

Accordingly, purification treatment for the dehydrated and distilled anhydrosugar alcohol is essential, but thereby the overall process becomes complicated, production cost increases, and the yield decreases due to the loss in the purification step.

The required purities of anhydrosugar alcohol are different according to the use thereof. In the case of use for foods or drugs, impurities harmful to the human body should not exist. In the case of use for polymers requiring optical transparency, the impurities which cause color formation or colorization during the synthesis and processing should not be contained. In addition, the impurities which undesirably increase or decrease the polymerization degree or polymerization rate during polymer synthesis should not be contained, either. Even if the impurity content is allowable for foods and drugs, it may not be allowed in polymer synthesis since the color formation or the change of polymerization property may be caused.

In particular, when anhydrosugar alcohol is used in the process of synthesizing plastics, etc., high ion content in anhydrosugar alcohol makes control of the polymerization rate difficult. Thus, ion content in anhydrosugar alcohol is an important factor for the application of anhydrosugar alcohol, but an efficient purification method for reducing it is hard to find.

Several methods of purifying anhydrosugar alcohol are generally known. One of them is a method of crystalizing anhydrosugar alcohol distillate by using an organic solvent. However, in the case of using anhydrosugar alcohol purified by this method in polymer synthesis, if the organic solvent is removed insufficiently, the remaining organic solvent may cause a change in the polymerization property. In addition, this method is not preferable since it has problems of insufficient removal of color-forming substances, requiring extra costs for facility and operation for crystallization, environmental harmfulness and unstable handling due to the use of organic solvent, etc. As an alternative, a method of crystallization using water as a solvent has been known, but there are problems of low efficiency of impurity removal and serious lowering of yield due to high hydrophilicity of anhydrosugar alcohol.

A method of purifying anhydrosugar alcohol distillate by using ion exchange resin and active carbon is also known. For instance, Korean Patent No. 10-0772255 discloses a method of treating anhydrosugar alcohol distillate with an adsorbent such as active carbon, etc., subsequently treating it with ion exchange resin, and further treating it with an adsorbent such as active carbon, etc. again. However, the purification method disclosed in this patent requires multiple processes of adsorption-ion exchange-adsorption, and even though purified as such, the final anhydrosugar alcohol has a relatively high conductivity of about 20 μs/cm or less. Furthermore, this patent makes no mention about the color property of the finally purified anhydrosugar alcohol.

Therefore, a technology of purifying anhydrosugar alcohol, which can remarkably reduce the ion content and the conductivity and improve the color property while reducing cost through more simplified process, is still required.

CONTENTS OF THE INVENTION

Problems to be Solved

To resolve the problems of the prior arts as explained above, the present invention has an object of providing a method for producing anhydrosugar alcohol which can remarkably reduce the ion content and the conductivity and improve the color property while reducing cost through a simplified process, and thus is suitable for a mass-production process on a commercial scale.

Technical Means

To achieve the above-stated object, the present invention provides a method for producing anhydrosugar alcohol comprising the steps of: (1) converting hydrogenated sugar to anhydrosugar alcohol by dehydration reaction, (2) distilling the resulting liquid of the reaction of said step (1), (3) contacting the resulting distillate of said step (2) with active carbon having an average particle size of from 0.2 mm to 1.0 mm, (4) contacting the resulting product of said step (3) with cationic ion exchange resin, and (5) contacting the resulting product of said step (4) with anionic ion exchange resin.

Effect of the Invention

According to the present invention, it is possible to produce anhydrosugar alcohol having remarkably reduced ion content, remarkably low conductivity and improved color property, which preferably has an ion content of 10 ppm or less (more preferably 1 ppm or less), a conductivity of 10 μs/cm or less, a color index b value of 0.2 or less (more preferably 0.05 or less) and a yellow index (YI) value of 0.1 or less, through a more simplified process using the existing facilities and columns without adding further facilities or procedures. In addition, the method for producing anhydrosugar alcohol of the present invention does not use an organic solvent and so is environmentally friendly, and can improve the yield and so is economical and suitable for a mass-production process on a commercial scale.

Concrete Explanation to Carry Out the Invention

The present invention is explained in more detail below.

The method for producing anhydrosugar alcohol of the present invention comprises a step of converting hydrogenated sugar to anhydrosugar alcohol by dehydration reaction [step (1)].

The hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar in one or more steps by any method.

In the present invention, hexitol is preferably used as the hydrogenated sugar, and more preferably, the hydrogenated sugar for use is selected from sorbitol, mannitol, iditol and mixtures thereof.

Accordingly, in the present invention, dianhydrohexitol—which is the dehydrated product of hexitol—is preferably obtained as the anhydrosugar alcohol, and more preferably, the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

The hydrogenated sugar is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol, and more preferably, an acid mixture of a first acid and a second acid can be used. As for the acid catalyst, in the case of a single-acid catalyst, sulfuric acid, hydrochloric acid, phosphoric acid, etc. can be used; and in the case of an acid mixture, sulfuric acid can be used as the first acid, and one or more sulfur-containing acids or salts thereof selected from the group consisting of p-toluenesulfonic acid, methanesulfonic acid, ethanesulfonic acid, benzenesulfonic acid, naphthalenesulfonic acid and aluminum sulfate can be used as the second acid. The acid catalyst is preferably used in an amount of from 0.5 to 10 parts by weight per 100 parts by weight of the hydrogenated sugar (e.g., hexitol). If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

According to an embodiment of the present invention, the step of converting hydrogenated sugar to anhydrosugar alcohol may be conducted in the presence of an acid catalyst as explained above, at a temperature of from 100° C. to 190° C. under a pressure of 20 mmHg or less for 1 hour to 10 hours.

In the case of using an acid catalyst during the dehydration reaction of hydrogenated sugar, it is preferable to neutralize the reaction product liquid. After the dehydration reaction, the neutralization may be conducted by cooling the reaction product liquid (e.g., to 100° C. or lower) and adding thereto conventional alkali such as sodium hydroxide. The neutralized reaction product liquid preferably has a pH of 6 to 8.

According to a preferable embodiment of the method for producing anhydrosugar alcohol of the present invention, the resulting liquid of the step of converting hydrogenated sugar to anhydrosugar alcohol may be pre-treated before being fed to the distilling step. The purpose of the pre-treatment is to remove moisture and a low-boiling-point substance(s) remaining in the resulting liquid of the converting step, and may be conducted conventionally at a temperature of from 90° C. to 110° C. under a pressure of 10 mmHg to 100 mmHg for 1 hour or longer (e.g., 1 to 4 hours), but it is not limited thereto.

In the method for producing anhydrosugar alcohol of the present invention, the resulting liquid of the reaction of step (1) is then distilled [step (2)]. There is no special limitation in the method and device for the distillation, and any conventionally known method and device in this field may be utilized as it is or with proper modification. For example, a general condenser type evaporator may be used, or a thin-film evaporator may be utilized for the distillation.

The distillate obtained as the result of step (2) is decolorized by contacting it with active carbon having an average particle size of from 0.2 mm to 1.0 mm, and more preferably from 0.25 mm to 0.75 mm [step (3)].

There is no special limitation in the manner of contacting the distillate with active carbon. For example, the contact may be conducted in a manner of passing the distillate through a column packed with the active carbon, or it may alternatively be conducted in a manner of incorporating the distillate and the active carbon into a reactor and mixing them with agitation for a given time. According to a preferable embodiment of the present invention, the decolorization treatment is conducted in a manner of passing the distillate through a column packed with the active carbon.

As the active carbon, one or more selected from active carbon groups obtained by activating a plant source such as wooden material, palm, etc. or a mineral source such as brown coal, bituminous coal, soft coal, anthracite coal, etc. may be used. There is no special limitation in the form of active carbon particle, and fine granular active carbon (e.g., average particle size of from 0.25 to 0.75 mm), granular active carbon (e.g., average particle size of 0.75 mm or greater), powder active carbon (e.g., average particle size of 0.25 mm or less), etc. may be used. According to a preferable embodiment of the present invention, fine granular active carbon is used. In order to increase the active carbon's efficiency, pre-treated (e.g., washed) active carbon may be used.

If the active carbon particles are so small that the average particle size is less than 0.2 mm, in the case of decolorization on a column, the flow rate decreases greatly and the pressure in the column increases, which is problematical. On the other hand, if the active carbon particles are so large that the average particle size is greater than 1.0 mm, the ion content and conductivity of the resulting anhydrosugar alcohol increase and the color index also increases, which is problematical, too.

The decolorized resulting liquid obtained in step (3) is then contacted with cationic ion exchange resin [step (4)].

The contact of the decolorized resulting liquid with cationic ion exchange resin may be conducted in a manner of passing the decolorized resulting liquid through a column packed with the ion exchange resin. As the cationic ion exchange resin, all of strong cationic ion exchange resin (e.g., TRILITE-SCR-B) and weak cationic ion exchange resin (e.g., DIAION WK11) may be used, and strong cationic ion exchange resin is preferably used. As the strong cationic ion exchange resin, one or more selected from H-form strong cationic ion exchange resin (e.g., TRILITE-SCR-BH) and Na-form strong cationic ion exchange resin (e.g., TRILITE-SCR-B) may be used preferably.

The resulting liquid obtained in step (4) is then contacted with anionic ion exchange resin [step (5)].

The contact of the resulting liquid of step (4) with anionic ion exchange resin may be conducted in a manner of passing the resulting liquid through a column packed with the ion exchange resin. As the anionic ion exchange resin, all of strong anionic ion exchange resin (e.g., TRILITE AMP24) and weak anionic ion exchange resin (e.g., DIAION WA10) may be used, and strong anionic ion exchange resin is preferably used. As the strong anionic ion exchange resin, Cl-form strong anionic ion exchange resin (e.g., TRILITE AMP24) may be used preferably.

There is no special limitation in the method and column device for the ion purification using ion exchange resin, and any conventionally known method and device in this field may be utilized as it is or with proper modification.

Unlike the above-explained order of ion purification, if anhydrosugar alcohol is treated with anionic ion exchange resin and then with cationic ion exchange resin, the resulting product of treatment has a low pH of 3 to 4 and thus a neutralizing agent should be added for its neutralization, by which additional ions are incorporated into the purification product, resulting in an increase of ion content and electric conductivity. Therefore, it is preferable that the ion purification be conducted in the order of cationic ion exchange resin treatment—anionic ion exchange resin treatment.

The present invention may further comprise, if necessary, a step of concentrating and crystalizing the anhydrosugar alcohol obtained as the result of step (5). However, even without conducting such a crystallization step, it is possible to obtain anhydrosugar alcohol having high purity, low ion content and low conductivity.

If anhydrosugar alcohol is purified according to a preferable embodiment of the present invention, it is possible to obtain anhydrosugar alcohol having remarkably reduced ion content, remarkably low conductivity and improved color property, which has an ion content of 10 ppm or less (more preferably 1 ppm or less, e.g., 0.01 ppm to 1 ppm), a conductivity (the lower, the better) of 10 μs/cm or less (e.g., 0.01 to 10 μs/cm), a color index b value of 0.2 or less (more preferably 0.05 or less, e.g., 0.01 to 0.05) and a yellow index (YI) value of 0.1 or less (e.g., 0.01 to 0.1).

The present invention is explained in more detail through the following Examples and Comparative Examples. However, the Examples are intended to facilitate understanding of the present invention only, and the scope of the present invention is not limited thereby.

EXAMPLES AND COMPARATIVE EXAMPLES

<Property Measurement>

The purity analysis of anhydrosugar alcohol was carried out by using gas chromatography (GC, HP6890). The ion content analysis was carried out by using an ion chromatograph (Dionex ICS-3000) and the electric conductivity measurement was carried out by using a conductivity meter (Pharmacia Biotech 18-1500). The color analysis was carried out by using color spectrometers (Hunterlab Ultrascan vis).

Example 1

1,200 g of sorbitol powder (D-sorbitol, Samyang Genex Inc.) was fed into a four-neck glass reactor equipped with an agitator and melted by heating to 110° C. 12 g of concentrated sulfuric acid (Duksan Chemical, 95%) and 7.2 g of methanesulfonic acid (Sigma, 70%) were added thereto, and the reaction mixture was heated to 135° C. In maintaining this temperature, dehydration reaction was conducted for 4 hours under a vacuum condition of 10 torr to convert the starting material, sorbitol, to the anhydrosugar alcohol, isosorbide. After the dehydration reaction, the reaction mixture was cooled to 110° C., and 31.2 g of 50% sodium hydroxide solution (Samjeon Pure Chemical) was added thereto to neutralize the resulting reaction liquid. The neutralized anhydrosugar alcohol was distilled by using a thin-film evaporator at 180° C. under vacuum of 5 torr or less. The purity of the obtained anhydrosugar alcohol distillate was 98.5%.

The obtained distillate was dissolved by adding distilled water thereto, and a solution with solid content of 55% was prepared. The prepared solution was decolorized by passing it through a column packed with fine granular active carbon having average particle size of 0.35 mm at the rate of 1.0 BV/h (bed volume/hour), and the decolorized anhydrosugar alcohol was then passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 0.9 ppm as the total of cation content and anion content, the conductivity was 3 µs/cm or less, and as the color property, the b value was 0.03 and the YI value was 0.07.

Example 2

The anhydrosugar alcohol distillate obtained in Example 1 (purity: 98.5%) was dissolved by adding distilled water thereto, and a solution with solid content of 55% was prepared. Powder active carbon having average particle size of 0.25 mm was added thereto in an amount of 1% based on the total dry weight of anhydrosugar alcohol, and the decolorization treatment was conducted by agitating the resulting mixture at 30° C. for 1 hour and filtering. The decolorized anhydrosugar alcohol was then passed through a column packed with Na-form strong cationic ion exchange resin (TRILITE-SCR-B, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 9.2 ppm as the total of cation content and anion content, the conductivity was 9 µs/cm or less, and as the color property, the b value was 0.15 and the YI value was 0.28.

Comparative Example 1

The anhydrosugar alcohol distillate obtained in Example 1 (purity: 98.5%) was dissolved by adding distilled water thereto, and a solution with solid content of 55% was prepared. The prepared solution was passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, and the resulting liquid was then passed through a column packed with fine granular active carbon having average particle size of 0.35 mm at the rate of 1.0 BV/h (bed volume/hour), to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 10.2 ppm as the total of cation content and anion content, the conductivity was 12 µs/cm or less, and as the color property, the b value was 0.03 and the YI value was 0.07.

Comparative Example 2

The anhydrosugar alcohol distillate obtained in Example 1 (purity: 98.5%) was dissolved by adding distilled water thereto, and a solution with solid content of 55% was prepared. The prepared solution was decolorized by passing it through a column packed with granular active carbon having average particle size of 1.5 mm at the rate of 1.0 BV/h (bed volume/hour), and the decolorized anhydrosugar alcohol was then passed through a column packed with Na-form strong cationic ion exchange resin (TRILITE-SCR-B, Samyang Corporation) at the rate of 1.5 BV/h, and the resulting liquid was then passed through a column packed with Cl-form strong anionic ion exchange resin (TRILITE AMP24, Samyang Corporation) at the rate of 1.5BV/h, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 10.8 ppm as the total of cation content and anion content, the conductivity was 11 µs/cm or less, and as the color property, the b value was 1.18 and the YI value was 1.87.

Comparative Example 3

The anhydrosugar alcohol distillate obtained in Example 1 (purity: 98.5%) was dissolved by adding distilled water thereto, and a solution with solid content of 55% was prepared. The prepared solution was decolorized by passing it through a column packed with granular active carbon having average particle size of 1.5 mm at the rate of 1.0 BV/h (bed volume/hour), and the decolorized anhydrosugar alcohol was then passed through a column packed with weak cationic ion exchange resin (DIAION WK11, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 12.1 ppm as the total of cation content and anion content, the conductivity was 14 µs/cm or less, and as the color property, the b value was 1.20 and the YI value was 1.92.

Comparative Example 4

The anhydrosugar alcohol distillate obtained in Example 1 (purity: 98.5%) was dissolved by adding distilled water thereto, and a solution with solid content of 55% was prepared. The prepared solution was decolorized by passing it through a column packed with granular active carbon having average particle size of 1.5 mm at the rate of 1.0 BV/h (bed volume/hour), and the decolorized anhydrosugar alcohol was then passed through a column packed with Na-form strong cationic ion exchange resin (TRILITE-SCR-B, Samyang Corporation) at the rate of 1.5 BV/h, and the resulting liquid was then passed through a column packed with weak anionic ion exchange resin (DIAION WA10, Samyang Corporation) at the rate of 1.5 BV/h, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 12.0 ppm as the total of cation content and anion content, the conductivity was 14 μs/cm or less, and as the color property, the b value was 1.19 and the YI value was 1.90.

Comparative Example 5

The anhydrosugar alcohol distillate obtained in Example 1 (purity: 98.5%) was dissolved by adding distilled water thereto, and a solution with solid content of 55% was prepared. The prepared solution was passed through a column packed with Na-form strong cationic ion exchange resin (TRILITE-SCR-B, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h. To the resulting liquid, powder active carbon having average particle size of 0.25 mm was added in an amount of 1% based on the total dry weight of anhydrosugar alcohol, and the decolorization treatment was conducted by agitating the resulting mixture at 30° C. for 1 hour and filtering, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 22.5 ppm as the total of cation content and anion content, the conductivity was 16 μs/cm or less, and as the color property, the b value was 0.10 and the YI value was 0.18.

Comparative Example 6

The anhydrosugar alcohol distillate obtained in Example 1 (purity: 98.5%) was dissolved by adding distilled water thereto, and a solution with solid content of 55% was prepared. The prepared solution was decolorized by passing it through a column packed with granular active carbon having average particle size of 1.5 mm at the rate of 1.0 BV/h (bed volume/hour), and the decolorized anhydrosugar alcohol was then passed through a column packed with Na-form strong cationic ion exchange resin (TRILITE-SCR-B, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h. To the resulting liquid, powder active carbon having average particle size of 0.25 mm was added in an amount of 1% based on the total dry weight of anhydrosugar alcohol, and the decolorization treatment was conducted by agitating the resulting mixture at 30° C. for 1 hour and filtering, to obtain the finally purified anhydrosugar alcohol.

The purified anhydrosugar alcohol was diluted with distilled water to 5.7% to analyze its ion content. The conductivity and color were analyzed and evaluated by diluting it with distilled water to 20%. As results of the analysis, the ion content was 25.5 ppm as the total of cation content and anion content, the conductivity was 17 μs/cm or less, and as the color property, the b value was 0.08 and the YI value was 0.17.

The ion content, conductivity and color property of each of the purified anhydrosugar alcohols obtained in the above Examples and Comparative Examples are summarized in the following Table 1.

TABLE 1

|  | Ion content (ppm) | Conductivity (μs/cm) | Color property | |
| --- | --- | --- | --- | --- |
|  |  |  | b value | YI value |
| Example 1 | 0.9 | 3 or less | 0.03 | 0.07 |
| Example 2 | 9.2 | 9 or less | 0.15 | 0.28 |
| Comparative Example 1 | 10.2 | 12 or less | 0.03 | 0.07 |
| Comparative Example 2 | 10.8 | 11 or less | 1.18 | 1.87 |
| Comparative Example 3 | 12.1 | 14 or less | 1.20 | 1.92 |
| Comparative Example 4 | 12.0 | 14 or less | 1.19 | 1.90 |
| Comparative Example 5 | 22.5 | 16 or less | 0.10 | 0.18 |
| Comparative Example 6 | 25.5 | 17 or less | 0.08 | 0.17 |

As can be seen from Table 1, the purified anhydrosugar alcohols produced according to the working examples of the present invention had an ion content of 10 ppm or less (more preferably, 1 ppm or less), a conductivity of 10 μs/cm or less, a color index b value of 0.2 or less (more preferably, 0.05 or less), and a YI value of 0.1 or less, satisfying remarkably reduced ion content, remarkably low conductivity and improved color property at the same time.

The invention claimed is:

1. A method for producing anhydrosugar alcohol comprising the steps of:
   (1) converting hydrogenated sugar to anhydrosugar alcohol by dehydration reaction,
   (2) distilling the resulting liquid of the reaction of said step (1),
   (3) contacting the resulting distillate of said step (2) with active carbon having an average particle size of from 0.25 mm to 0.75 mm,
   (4) contacting the resulting product of said step (3) with cation ion exchange resin, and
   (5) contacting the resulting product of said step (4) with anion ion exchange resin,
   wherein the method does not comprise a further step of treating the resulting product of said step (5) with active carbon, and
   wherein the produced anhydrosugar alcohol has an ion content of 10 ppm or less, a conductivity of 10 μs/cm or less, a color index b value of 0.2 or less, and a yellow index (YI) value of 0.1 or less.

2. The method for producing anhydrosugar alcohol according to claim 1, wherein the hydrogenated sugar is hexitol and the anhydrosugar alcohol is dianhydrohexitol.

3. The method for producing anhydrosugar alcohol according to claim 1, wherein an acid catalyst is used in the step of converting hydrogenated sugar to anhydrosugar alcohol by dehydration reaction.

4. The method for producing anhydrosugar alcohol according to claim 1, wherein in said step (3), the contact of the resulting distillate of step (2) with active carbon is conducted by passing the distillate through a column packed with the active carbon.

5. The method for producing anhydrosugar alcohol according to claim 1, wherein in said step (3), the contact of the resulting distillate of step (2) with active carbon is conducted by incorporating the distillate and the active carbon into a reactor and mixing them with agitation.

6. The method for producing anhydrosugar alcohol according to claim 1, wherein the active carbon is one or more selected from active carbon groups obtained by activating plant source or mineral source.

7. The method for producing anhydrosugar alcohol according to claim 1, wherein the cation ion exchange resin used in said step (4) is a strong cation ion exchange resin.

8. The method for producing anhydrosugar alcohol according to claim 7, wherein the strong cationic ion exchange resin is one or more selected from H-form strong cation ion exchange resin and Na-form strong cation ion exchange resin.

9. The method for producing anhydrosugar alcohol according to claim 1, wherein the anion ion exchange resin used in said step (5) is a strong anion ion exchange resin.

\* \* \* \* \*